US009414854B1

(12) United States Patent
Gordon

(10) Patent No.: US 9,414,854 B1
(45) Date of Patent: Aug. 16, 2016

(54) OVARIAN LIGAMENT SHEAR

(76) Inventor: Hylton P. Gordon, White Plains, NY (US)

( * ) Notice: Subject to any disclaimer, the term of this patent is extended or adjusted under 35 U.S.C. 154(b) by 196 days.

(21) Appl. No.: 13/524,119

(22) Filed: Jun. 15, 2012

(51) Int. Cl.
A61B 17/32 (2006.01)
A61B 17/3201 (2006.01)

(52) U.S. Cl.
CPC .................... A61B 17/3201 (2013.01)

(58) Field of Classification Search
CPC ............... A61B 17/285; A61B 17/295; A61B 17/2955; A61B 17/320092
See application file for complete search history.

(56) References Cited

U.S. PATENT DOCUMENTS

| 5,176,695 | A | 1/1993 | Dulebohn | |
| 5,203,785 | A | 4/1993 | Slater | |
| 5,211,655 | A | 5/1993 | Hasson | |
| 5,219,354 | A * | 6/1993 | Choudhury et al. | 606/174 |
| 5,569,298 | A | 10/1996 | Schnell | |
| 8,628,557 | B2 * | 1/2014 | Collings et al. | 606/205 |
| 2005/0192633 | A1 * | 9/2005 | Montpetit | 606/232 |

* cited by examiner

Primary Examiner — Melanie Tyson
Assistant Examiner — Todd J Scherbel

(57) ABSTRACT

An ovarian ligament shear that includes a blade pivotally disposed upon a perhensile section, said prehensile section disposed at a distal end of a foremember, and a securing clasp pivotally disposed proximal the blade, each of the blade and the securing clasp moveable by means of each of a respective first cable and second cable disposed within an interior cavity, said first and second cables rotationally torqued by a pivot pin rotatably disposed in a center-piece, said pin attached to a second handle member, wherein the second handle member rotates the pivot pin when the second handle member is moved between an open position and a closed position, whereby each of the blade and the securing clasp are moved from a first position to a second position and a pedicle is securable and severable thereby.

8 Claims, 5 Drawing Sheets

OVARIAN LIGAMENT SHEAR

BACKGROUND OF THE INVENTION

Various types of ligament shears are known in the prior art. However, what is needed is an ovarian ligament shear that includes a blade pivotally disposed on a perhensile section, said prehensile section disposed at a distal end of a foremember, and a securing clasp pivotally disposed proximal to the blade, each of the blade and the securing clasp moveable by means of each of a respective first cable and second cable disposed within an interior cavity, said first and second cables rotationally torqued by a pivot pin rotatably disposed in a center-piece, said pin attached to a second handle member, wherein the second handle member rotates the pivot pin when the second handle member is moved between an open position and a closed position, whereby each of the blade and the securing clasp are moved from a first position to a second position and a pedicle is securable and severable thereby.

FIELD OF THE INVENTION

The present invention relates to an ovarian ligament shear, and more particularly, to an ovarian ligament shear that includes a blade pivotally disposed on a perhensile section, said prehensile section disposed at a distal end of a foremember, and a securing clasp pivotally disposed proximal the blade, each of the blade and the securing clasp moveable by means of each of a respective first cable and second cable disposed within an interior cavity, said first and second cables rotationally torqued by a pivot pin rotatably disposed in a center-piece, said pin attached to a second handle member, wherein the second handle member rotates the pivot pin when the second handle member is moved between an open position and a closed position, whereby each of the blade and the securing clasp are moved from a first position to a second position and a pedicle is securable and severable thereby.

SUMMARY OF THE INVENTION

The general purpose of the ovarian ligament shear, described subsequently in greater detail, is to provide an ovarian ligament shear which has many novel features that result in an ovarian ligament shear which is not anticipated, rendered obvious, suggested, or even implied by prior art, either alone or in combination thereof.

Spaying pets requires an ovariectomy or an ovariohysterectomy, procedures involving major surgery. A laparotomy is performed, the ovary located, the pedicle isolated, ligated, and severed. Spaying is a common procedure actively encouraged in the modern day, and a majority of surgeries likely to be performed by a veterinarian include ovariectomies. An easier way of isolating and subsequently severing the pedicle of a pet being spayed is warranted, to decrease time, risk of accidents, and opportunistic infection or post operative infection resulting therefrom.

The present ovarian ligament shear has been devised to enable a veterinarian to readily locate, isolate, and sever a pedicle when spaying a pet. The present ovarian ligament shear includes a first handle member connected to a center-piece and a foremember disposed at an approximately 45 degree decline with respect to the center-piece. A second handle member is pivotally attached to the center-piece by means of a pivot pin. The pivot pin is attached to the second handle member and is rotatably disposed in the center-piece. The second handle member rotatably engages the pivot pin when the second handle is moved between an open position and a closed position.

A prehensile section is disposed upon a distal end of the foremember. The prehensile section includes an anvil member, a blade, and a securing clamp. The anvil member is an arced endpiece disposed in a perpendicular plane relative the foremember and is used to hook a pedicle and isolate said pedicle thereat. The blade is moveably disposed upon the prehensile section and is moveable between a first position and a second position. The blade has a cutting edge disposed to contact the anvil member when the blade is moved to the second position. The anvil member has a blade receiving groove disposed thereupon to receive and engage with the cutting edge when the blade is moved to the second position.

A securing clasp is moveably disposed on the prehensile section proximal the blade, the securing clasp moveable between a first position and a second position. The securing clasp engages with the anvil member when moved to the second position. A slit is disposed within the securing clasp, the slit configured to receive the blade therethrough when the securing clasp is moved to the second position. The securing clasp overlies the blade and releasably engages the pedicle against the anvil member when severing the pedicle to secure the pedicle in place.

To operationally control the blade and the securing clasp, a first cable and a second cable are disposed within an interior cavity disposed inside the foremember and the center-piece. Each of the first cable and second cable are operationally engaged by the rotation of the pivot pin when the second handle member is moved between the open position and the closed position. Thusly, the second handle member torques each of the first cable and the second cable when the second handle member is moved between the open position an the closed position.

The first cable is in operational communication with the blade. The blade is pivotally attached to the prehensile section. When the second handle member causes the pivot pin to rotate, the first cable member is torqued to pull the blade to the second position. The second cable is in operational communication with the securing clasp. In like manner, the second handle member torques the second cable and the second cable pulls the securing clasp to the second position. The securing clasp is also pivotally attached to the prehensile section. The disposition of the second cable relative the first cable ensures the movement of the securing clasp is synchronized with the movement of the blade, and the second cable may be configured to torque the securing clasp consecutively with, or previous or subsequent to, the movement of the blade.

Thus has been broadly outlined the more important features of the present ovarian ligament shear so that the detailed description thereof that follows may be better understood and in order that the present contribution to the art may be better appreciated.

Objects of the present ovarian ligament shear, along with various novel features that characterize the invention are particularly pointed out in the claims forming a part of this disclosure. For better understanding of the ovarian ligament shear, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
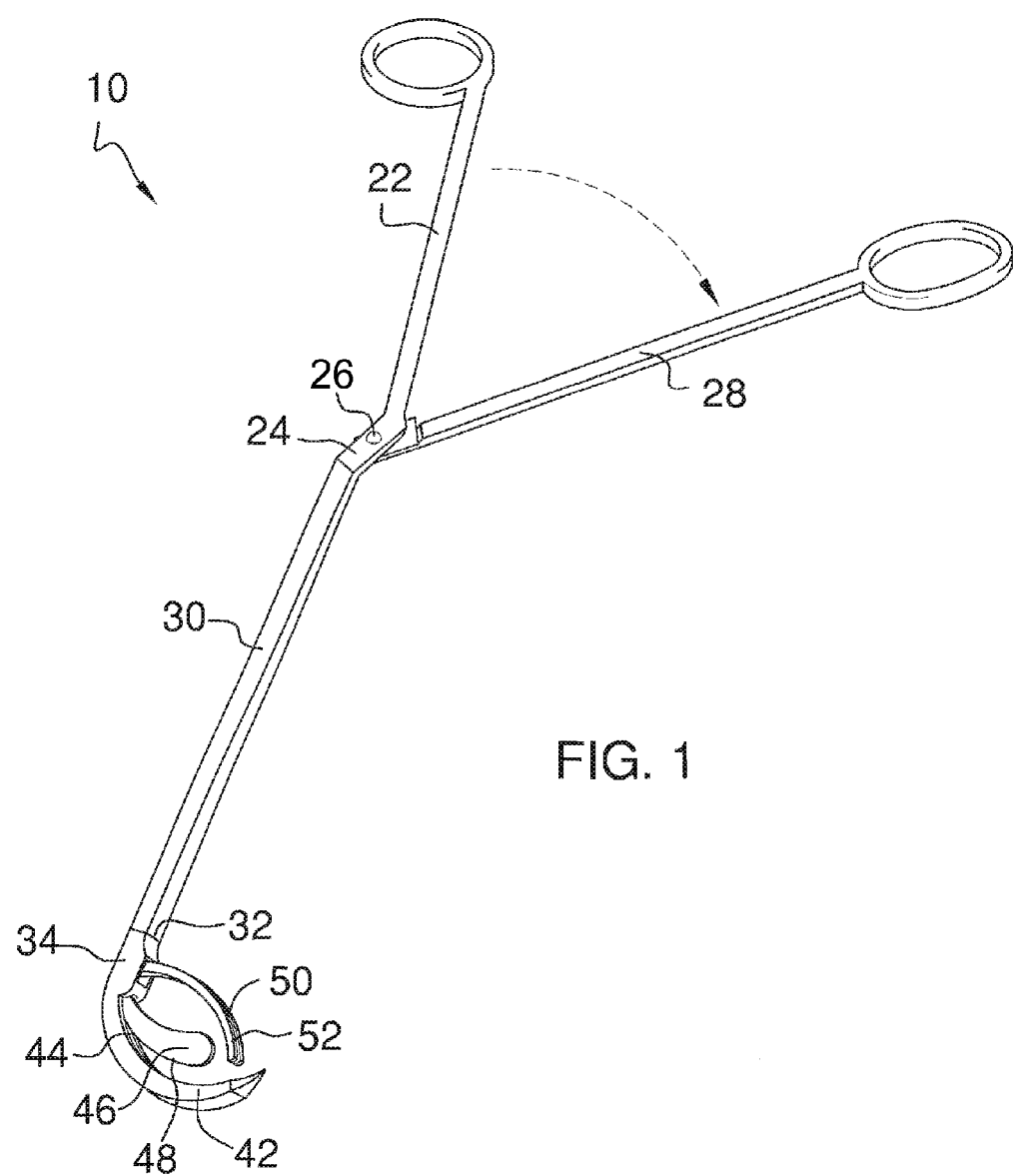
FIG. 1 is an isometric view.
Figure 2:
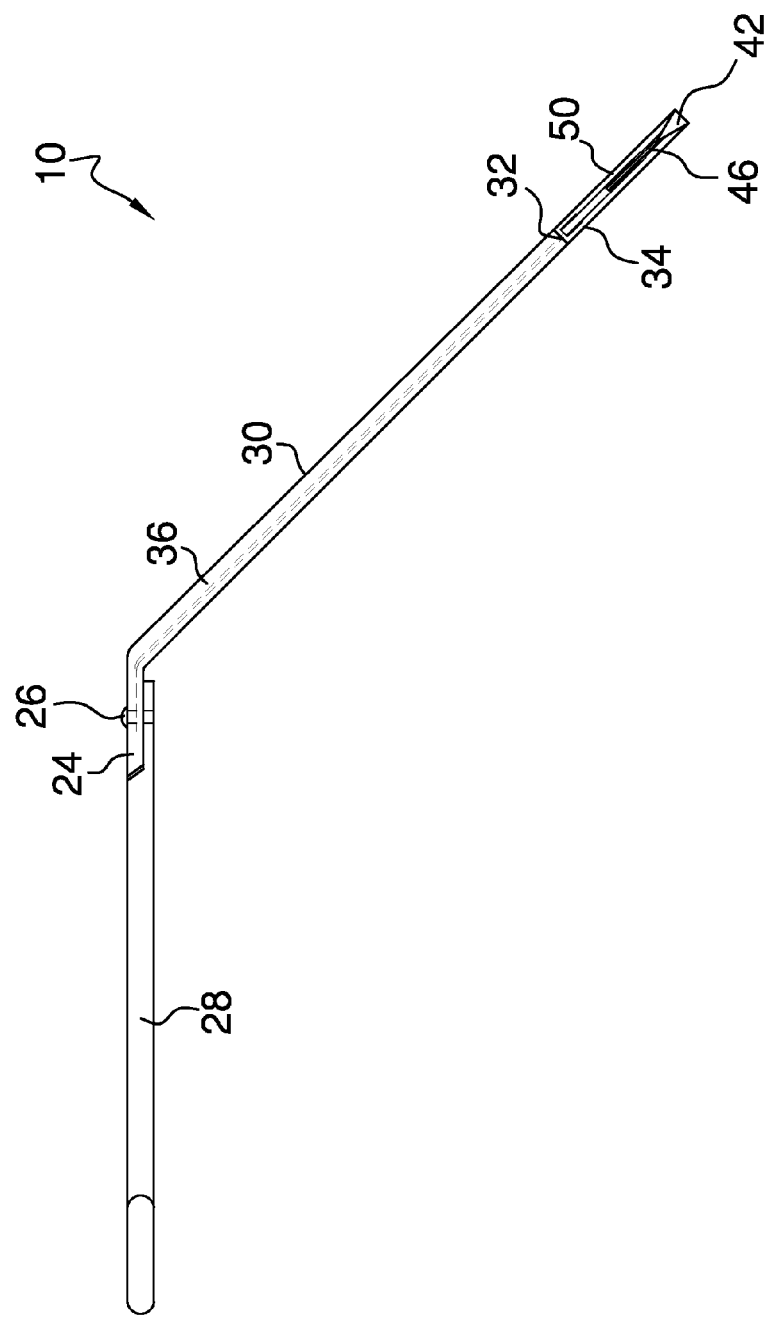
FIG. 2 is a side view.
Figure 3:
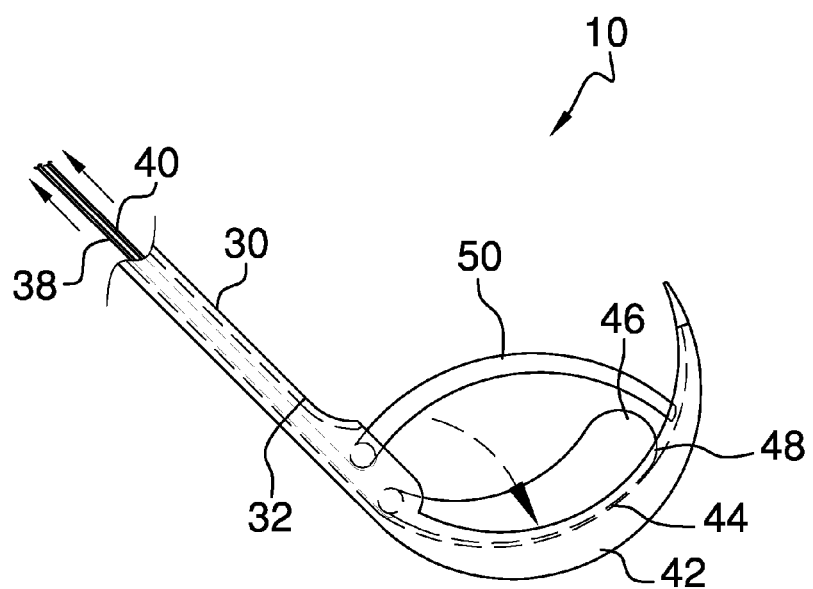
FIG. 3 is a detail view.
Figure 4:
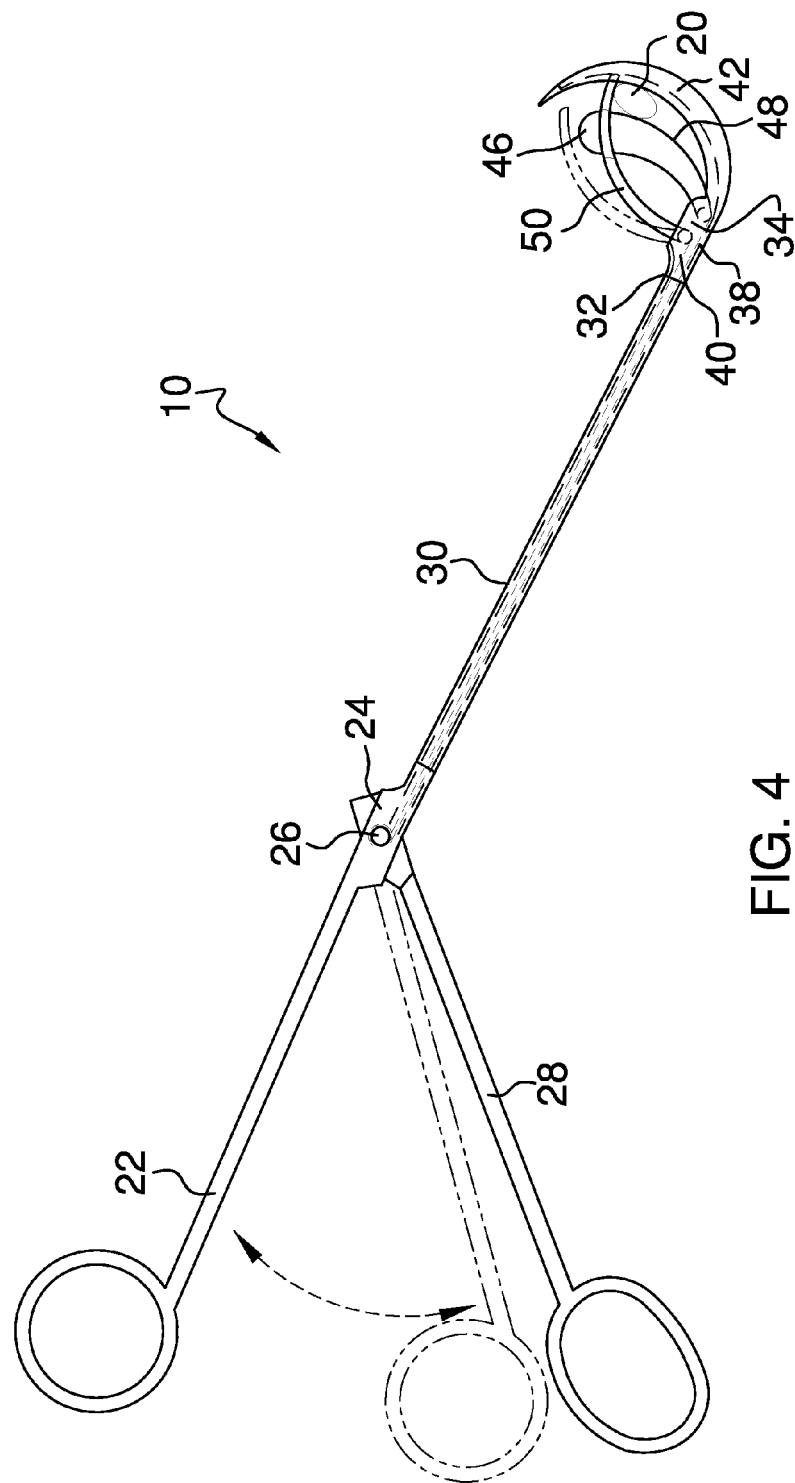
FIG. 4 is a top view.

With reference now to the drawings, and in particular FIGS. 1 through 5 thereof, example of the instant ovarian ligament shear employing the principles and concepts of the present ovarian ligament shear and generally designated by the reference number 10 will be described.

Referring to FIGS. 1 through 5 a preferred embodiment of the present ovarian ligament shear 10 is illustrated.

The ovarian ligament shear 10 is devised for use when performing an ovariectomy or an ovariohysterectomy. The instant ovarian ligament shear 10 more expediently severs ovarian ligaments while necessitating a smaller incision in the abdomen than the current procedure used when spaying animals in the typical way.

The present ovarian ligament shear 10 readily isolates the pedicle 20, which may then be ligated, severed, and the ovary removed with relative ease. The present ovarian ligament shear 10 includes a first handle member 22, a center-piece 24 disposed endwise upon the first handle member 22, a pivot pin 26 rotatably disposed in the center-piece 24, and a second handle member 28 attached to the pivot pin 26. The second handle member 28 rotationally engages the pivot pin 26 when the second handle member 28 is moved between an open position and a closed position.

An elongated foremember 30 is disposed endwise upon the center-piece 24. The foremember 30 is disposed at an approximately 45 degree decline relative the first handle member 22, the second handle member 28, and the center-piece 24. The declination of the foremember 30 enables proximity to the pedicle 20 without having to reach with the hands or a pair of surgical scissors beneath the ovary. The foremember 30 has a prehensile section 34 disposed at a distal end 32.

An interior cavity 36 is disposed within the foremember 30 and the center-piece 24. A first cable 38 and a second cable 40 are disposed within the interior cavity 36 in operational communication with the pivot pin 26. Each of the first cable 38 and the second cable 40 is rotationally engaged by the pivot pin 26 when the pivot pin 26 is rotated by the second handle member 28 moving between the open position and the closed position. Thusly each of the first and second cables 38, 40 is torqued by action of the second handle member 28.

A curved anvil member 42 is disposed endwise upon the prehensile section 34, the anvil member 42 disposed within a coronal plane relative the foremember 30. The anvil member 42 is an arced end piece used to hook around the pedicle 20 during the ovariectomy, and isolate the pedicle 20 thereat. A blade receiving groove 44 is disposed upon the anvil member 42.

A blade 46, proximal the anvil member 42, is moveably disposed upon the prehensile section 34 in a coronal plane relative the foremember 30. The blade 46 is moveable between a first position and a second position. A cutting edge 48 of the blade 46 engages with the blade receiving groove 44 of the anvil member 42 when the blade 46 is moved to the second position. The blade 46 is in operational communication with the first cable 38, and when the second handle member 28 is moved between the open position and the closed position the blade 46 is moved between the first position and the second position. Thusly, the anvil member 42 is used to isolate the pedicle 20 and the blade 46 is useable to sever the pedicle 20 by means of the second handle member 28 engaging the blade 46 to the second position against the anvil member 42.

A securing clasp 50 is moveably disposed upon the prehensile section 34 in a sagittal plane relative the foremember 30, the securing clasp 50 moveable between a first position and a second position. The securing clasp 50 overlies the blade 46. The securing clasp 50 is in operational communication with the second cable 40 and the securing clasp 50 engages with the anvil member 42 when the securing clasp 50 is moved to the second position. The securing clasp 50 thusly secures the pedicle 20 to the anvil member 42 for incision by the blade 46.

A slit 52 is disposed in the securing clasp 50, the slit 52 configured to receive the blade 46 therethrough when the securing clasp 50 is moved to the second position and the blade 46 moves to the second position. The pivot pin 26 rotates when the second handle member 28 is moved between a closed position and an open position, and the blade 46 and the securing clasp 50 are moved between the first position and the second position thereby. A pedicle 20 hooked by the anvil member 42 is therefore securable and incisible by means of the cutting edge 48 of the blade 46 mating with the blade receiving groove 44 of the anvil member 42 when the second handle member 28 is moved to the closed position.

The present ovarian ligament shear 10 is approximately six inches long and one-half inches wide. However, alternate sizes are considered for use with different animals, as desired. It should also be noted that the device 10 is useable with humans, if desired, and should not necessarily be limited to veterinarian use.

Figure 5:
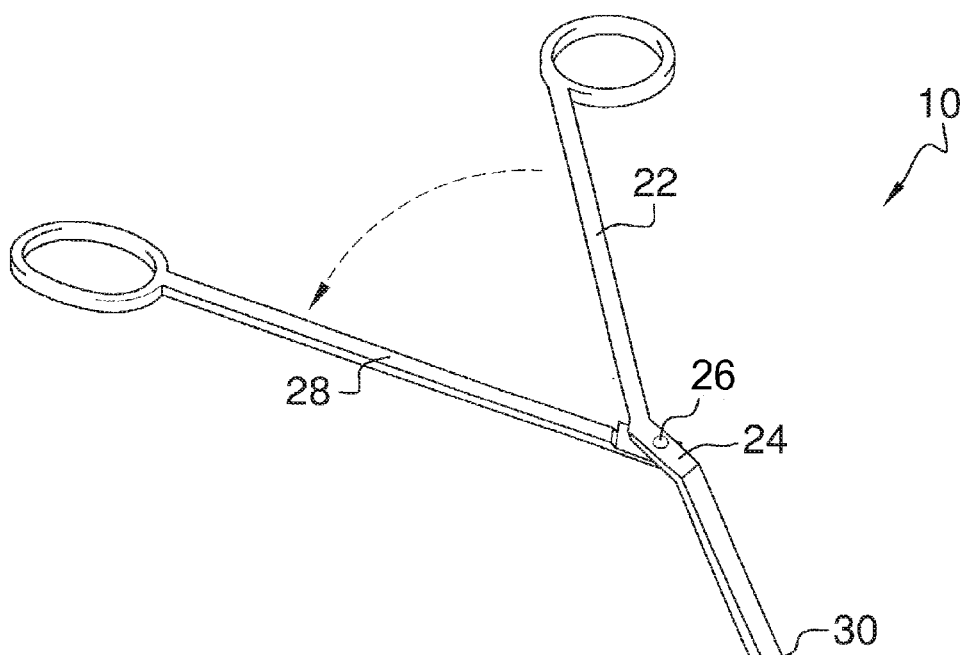
FIG. 5 is an isometric view of a left-handed version of the apparatus.

An embodiment of the present ovarian ligament shear 10 is illustrated in FIG. 5 for use by a left-handed surgeon, wherefore it should be readily realized that the orientation of the prehensile section 34 relative the foremember 30 should not be considered as limiting the device.

What is claimed is:

1. An ovarian ligament shear comprising:

a first handle member;

a center-piece disposed endwise upon the first handle member;

a second handle member pivotally attached to the center-piece;

an elongated foremember disposed endwise on the center-piece, said foremember disposed at approximately a 45 degree decline relative to the center-piece;

a curved anvil member disposed in a coronal plane with respect to the foremember, the anvil member disposed endwise upon the foremember;

a blade pivotally disposed proximal to the anvil member, the blade disposed in a coronal plane with respect to the foremember, said blade in operational communication with the first handle member and the second handle member, wherein the blade is configured to be moveable between a first position and a second position whereby the blade engages with the anvil member when the blade is moved to the second position;

a securing clasp disposed proximal the blade, the securing clasp disposed in a coronal plane with respect to the foremember, the securing clasp in operational communication with the first handle member and the second handle member wherein the securing clasp is moveable between a first position and a second position whereby the securing clasp engages with the anvil member when moved to the second position a pivot pin rotatably disposed in the center-piece, said pivot pin attached to the second handle member wherein the pivot pin is rotatable when the second handle member is moved between an open position and a closed position; and a first cable and a second cable in operational communication with the blade and the securing clasp respectively, each of the first cable and the second cable rotationally engaged by the pivot pin when said pivot pin rotates wherein the blade and the securing clasp are moveable between the first position and the second position when the second handle member is moved between the open position and the closed position.

2. The ovarian ligament shear of claim 1 wherein the blade is configured to be moveable between the first position when the first handle member and the second handle member are moved to an open position, and the second position when the first handle member and the second handle member are moved to a closed position, said blade engaging with the anvil member when the blade is moved to the second position.

3. The ovarian ligament shear of claim 2 wherein the securing clasp is configured to be moveable between the first position when the first handle member and the second handle member are moved to the open position, and the second position when the first handle member and the second handle member are moved to the closed position, said securing clasp engaging with the anvil member when the clasp is moved to the second position.

4. The securing clasp of claim 1 further comprising a slit configured to receive the blade therethrough when the clasp is moved to the second position.

5. The anvil member of claim 1 further comprising a blade receiving groove configured to receive the blade therein when the blade is moved to the second position.

6. The blade of claim 1 further comprising a cutting edge disposed to contact the anvil member when the blade is moved to the second position.

7. The ovarian ligament shear of claim 1 approximately 6 inches long and approximately half an inch wide.

8. An ovarian ligament shear for use when performing an ovariectomy comprising:
a first handle member;
a center-piece disposed endwise upon the first handle member;
a pivot pin rotatably disposed in the center-piece;
a second handle member attached to the pivot pin, the second handle member rotationally engaging the pivot pin when the second handle member is moved between an open position and a second position;
an elongated foremember disposed endwise upon the center-piece, said foremember disposed at approximately a 45 degree decline relative the first handle member, the second handle member, and the center-piece;
an interior cavity disposed within the foremember and the center-piece;
a first cable disposed within the interior cavity;
a second cable disposed within the interior cavity;
a prehensile section disposed endwise upon the foremember;
a curved anvil member disposed endwise upon the prehensile section, the anvil member disposed within a coronal plane relative the foremember;
a blade receiving groove disposed upon the anvil member;
a blade in operational communication with the first cable, said blade moveably disposed upon the prehensile section in a coronal plane relative the foremember, the blade moveable between a first position and a second position, the blade engaging with the blade receiving groove of the anvil member when said blade is moved to the second position;
a securing clasp in operational communication with the second cable, the securing clasp moveably disposed upon the prehensile section in a coronal plane relative the foremember, the securing clasp moveable between a first position and a second position, the securing clasp engaging with the anvil member when said clasp is moved to the second position;
a slit disposed in the securing clasp, said slit configured to receive the blade therethrough when the securing clasp is moved to the second position;
wherein the pivot pin rotates when the second handle member is moved between a closed position and an open position, the pivot pin rotationally engages each of the first and second cables, whereby the blade and the securing clasp are moved between the first position and the second position and a ligament hooked by the anvil member is securable and incisible thereat.

* * * * *